(12) United States Patent
Alesi

(10) Patent No.: US 6,309,376 B1
(45) Date of Patent: Oct. 30, 2001

(54) SAFETY DEVICE FOR INTRAVENOUS INFUSION NEEDLES

(75) Inventor: Daniel E. Alesi, Keene, NH (US)

(73) Assignee: Sims Portex, Inc., Keene, NH (US)

( * ) Notice: Subject to any disclaimer, the term of this patent is extended or adjusted under 35 U.S.C. 154(b) by 0 days.

(21) Appl. No.: 09/413,803

(22) Filed: Oct. 7, 1999

(51) Int. Cl.$^7$ ........................................... A61M 5/00
(52) U.S. Cl. ............................................................. 604/263
(58) Field of Search ................................. 604/192, 187, 604/263; 248/534, 540, 541

*Primary Examiner*—Manuel Mendez
(74) *Attorney, Agent, or Firm*—Louis Woo

(57) ABSTRACT

A safety device to be used with a winged intravenous infusion assembly has a base that is adaptable to fit over the body of the infusion assembly. Attached to the base is a housing that is pivotable to a position in substantial alignment along the longitudinal axis of the base for enveloping a needle extending from the infusion assembly when the housing is pivoted to the alignment position. Locking mechanisms may be provided in the housing for preventing movement of the housing relative to the needle once the needle is enveloped by the housing. The base can be configured to include a tubular portion that slidably fits over the front end of the infusion assembly or a pair of arms that intimately embrace the body of the infusion assembly. Alternatively, the safety device could be cast from the same mold as the IV infusion assembly so that the molded IV infusion assembly could have directly extending therefrom the safety device.

23 Claims, 4 Drawing Sheets

SAFETY DEVICE FOR INTRAVENOUS INFUSION NEEDLES

FIELD OF THE INVENTION

The present invention relates to needle protection devices and more particularly to a safety device adaptable to be used with an intravenous infusion needle.

BACKGROUND OF THE INVENTION

For intravenous (IV) infusions and/or withdrawing of venous blood, a device commonly known as a "butterfly" or winged intravenous infusion assembly is often used. This device may also be known as a hemodialysis needle.

Given the increasing risks of blood borne disease that a care giver, or for that matter a bystander, is exposed to when needle devices are used, some states have now mandate the use of protection devices that would preclude a contaminated needle from being exposed to the environment. Some of the currently available needle protection devices for IV infusion needles include the SAFETY-LOK blood collection sets manufactured by the Becton Dickinson Company and the ANGLWING safety needle protection system manufactured by the Sherwood Medical Company. These systems are sold as sets in that the needle protection device is already built onto the winged infusion assembly.

Yet there are standalone winged infusion assemblies. For those types of assemblies, there is therefore a need to provide or fit them with a safety device that would preclude the needle, after it has been contaminated with a patient's blood, from being exposed to the environment. Moreover, for ease of manufacture, it may be advantageous to mold the safety device and the IV infusion assembly as a single unit

SUMMARY OF THE PRESENT INVENTION

The present invention is a safety device that is adaptable to be used with various types of winged intravenous infusion assemblies. In addition, the present invention safety device also can lend itself to being integral with the molding of the IV butterfly wings. Specifically, the safety device of the instant invention can be used as an add-on device that has a base which is adaptable to be fitted to the body of a winged IV infusion assembly. The base is configured to have an interior surface that comes into intimate contact with the outside surface of the body of the winged IV infusion assembly so that, once the base of the safety device is fitted over the body of the infusion assembly, it is securely mounted thereto. Alternatively, the base can be an integral part of the body of the winged IV infusion assembly.

Attached to the side of the base that faces the needle that extends from the infusion assembly is a housing or sheath. The housing is hingedly attached to the base by, for example, a living hinge. The housing further has a groove or a passage extending substantially along the length thereof so that after the needle of the infusion device is removed from the patient, the housing can be pivoted to a position in substantial alignment along the longitudinal axis of the base to envelop the contaminated needle.

Locking mechanisms may be integrated to the housing for fixedly retaining the contaminated needle within the housing once the housing has been pivoted to the alignment position. Such locking mechanisms may include for example a hook or opposing fingers within the housing that act as a barrier for the removal of the housing from the needle. Locking mechanisms may also be used external of the housing for keeping the needle relatively fixed in relation to the housing. Such external locking mechanisms may include for example a side snap mechanism in which at least one locking means at the base would cooperate with a corresponding locking means external of the housing so that once the housing is pivoted to the alignment position, it is prevented from further movement from the alignment position.

The base of the safety device of the instant invention may be configured in two ways. First, it may be configured to have two pairs of extending arms each of which would snappingly secure to a corresponding portion of the body of the infusion assembly. Another embodiment of the instant invention provides a base that has a tubular section slidable over an end portion of the body of the infusion assembly for securing the base thereto. A pair of arms extending from the base may also be added to the tubular section embodiment for snappingly embracing yet another portion of the body of the infusion assembly to thereby even more securely mate the base of the safety device to the body of the infusion assembly. To further ensure that the base be securely coupled to the body of the infusion assembly, a coating of conventional adhesive may be sprayed or added to the interior surface of the base of the safety device so that, once the base is mounted to the body of the infusion assembly, it becomes bonded thereto.

It is therefore an objective of the present invention to provide a safety device that can easily be adapted to be used with a conventional intravenous infusion needle assembly.

It is yet another objective of the present invention to provide a safety device that can particularly be used to prevent a needle from a winged intravenous infusion needle assembly, once contaminated, from being exposed to the environment.

It is still another objective of the present invention to provide a one piece molded IV assembly with a built in safety device.

BRIEF DESCRIPTION OF THE FIGURES

The above-mentioned objectives and advantages of the present invention will become apparent and the invention itself will be best understood by reference to the following description of embodiments of the present invention taken in conjunction with the accompanying drawings, wherein.

DETAILED DESCRIPTION OF THE INVENTION

Figure 1:
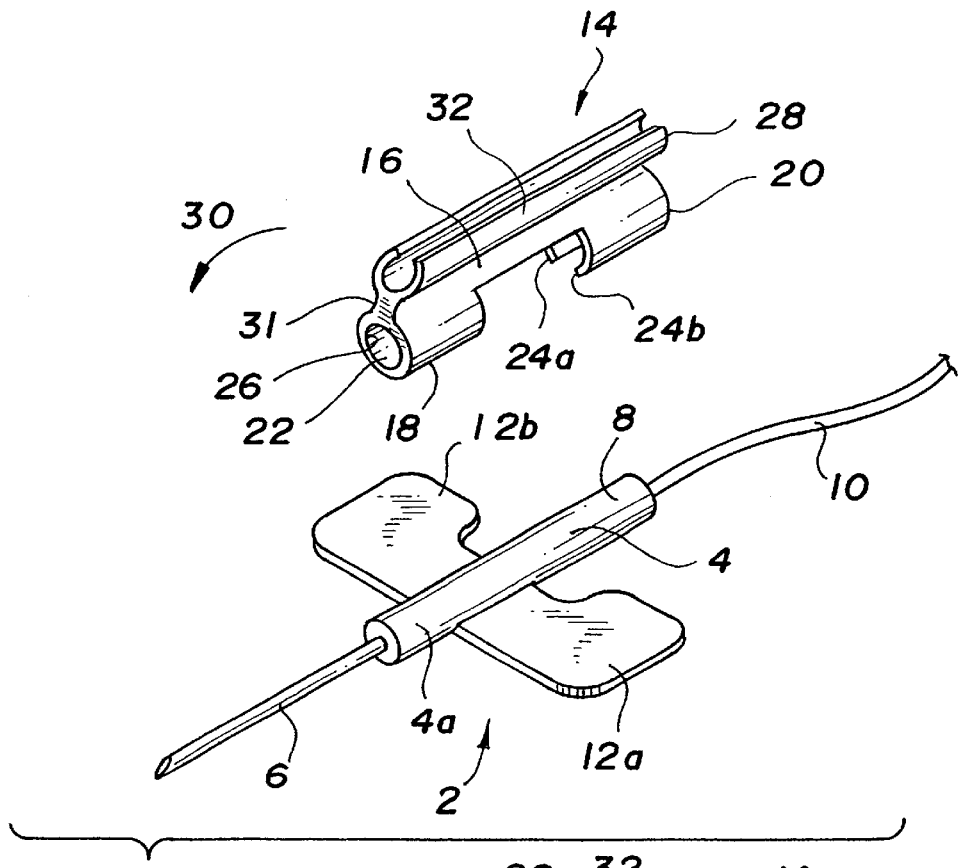
FIG. 1 is a perspective view of a first embodiment of the safety device of the present invention.

With reference to FIG. 1, a conventional winged intravenous infusion assembly 2 is shown to include a body 4 that has extending from one end thereof an intravenous needle 6. At the other end of body 4, which for the instant discussion is referred to as a hub 8, there is attached a flexible tubing 10. Extending in a direction perpendicular to the longitudinal axis of base 4 is a pair of wings 12a and 12b. For the sake of clarity, wing 12b is not fully shown. Insofar as winged intravenous infusion assembly 2 is well known, no further discussion thereof is deemed to be necessary.

The safety apparatus of the instant invention, which is to be added to winged intravenous infusion assembly 2, is shown in FIG. 1 as safety device 14. Safety device 14, as shown being superposed over infusion assembly 2, comprises a base 16 that is made up of a front portion 18 and an aft portion 20. For the embodiment shown in FIG. 1, the forward portion 18 of base 16 is a tubular section with an opening 22 that can be slideably fitted over needle 6 onto front end portion 4a of infusion assembly 2. Aft portion 20 of base 16 of safety device 14 of the FIG. 1 embodiment is comprised of a pair of arms 24a and 24b which, due to the characteristics of the plastic material used for molding safety device 14, are somewhat elastic. Thus, once tubular portion 18 is slideably fitted over section 4a of body 4, arms 24a and 24b will snappingly engage with hub 8 of body 4. And due to their elastic characteristics, once arms 24a and 24b are forcibly snapped over hub 8, they will intimately embrace hub 8 to thereby preclude their removal from hub 8.

The inner circumferential surface of body 6, designated 26, is configured to make intimate contact with the outer circumferential surface of body 4 so that, once fitted onto body 4, the inside surface of base 16 will intimately contact a substantial portion of body 4 of infusion assembly 2. To further ensure that base 16 would not separate from body 4 once the former is fitted onto the latter, a coating of conventional adhesive such as for example epoxy may be added to the interior surface of base 16 so that base 16 will bond to body 4 after it is appropriately fitted onto body 4. Note that to provide adequate bonding, only a given portion of the interior surface of base 6 may need to be coated with the appropriate adhesive, as it may not be necessary that all of the internal surfaces of base 16 be coated with the adhesive.

As further shown in the FIG. 1 embodiment, safety device 14 has hingedly connected to base 16 a housing 28. Housing 28 may be connected to base 16 by means of a living hinge 31. As shown, housing 28 has a groove 32 that extends along its length. Thus, once base 16 is fitted onto body 4 of infusion assembly 2, to prevent needle 16 from being exposed to the environment, the care giver only needs to pivot housing 28 in the direction as shown by directional arrow 30 to thereby envelop needle 6. Locking mechanisms, not shown in FIG. 1, would secure needle 6 within housing 28.

Figure 2:
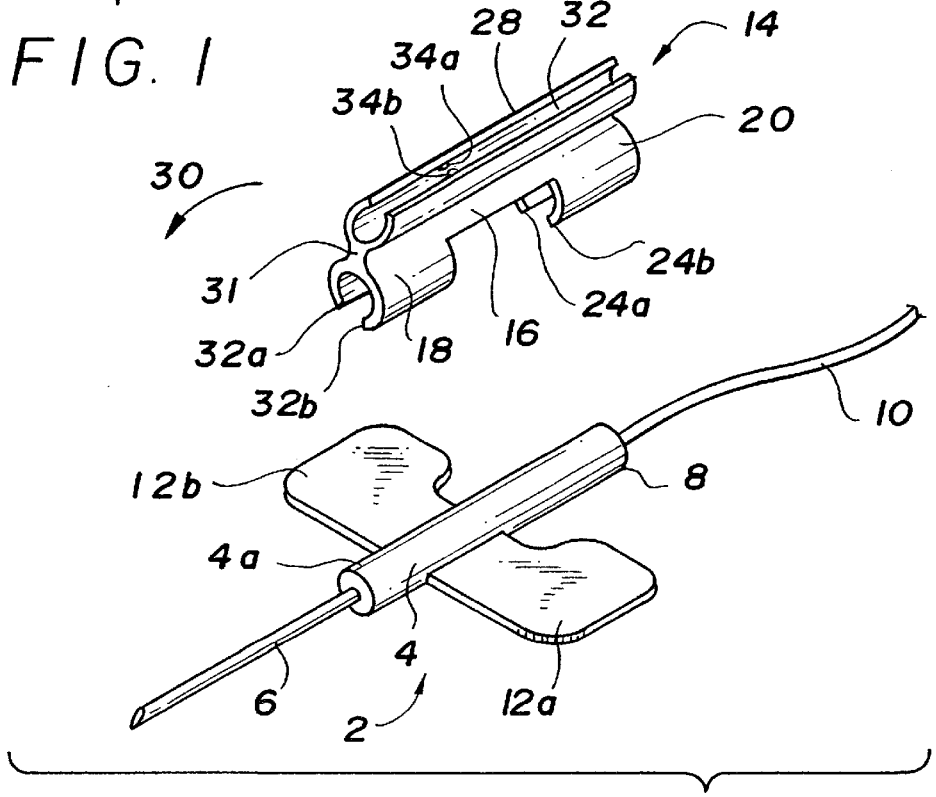
FIG. 2 is a perspective view of another embodiment of the safety device of the present invention.

FIG. 2 shows a second embodiment of the safety device of the instant invention. The same components shown in FIG. 2, as well as shown in the remaining drawings, that are the same as those shown in FIG. 1 are labeled with the same numerals. For the FIG. 2 embodiment, forward portion 18 of base 16, instead of being a tubular section, is seen to be made up of a pair of arms 32a and 32b. Arms 32a and 32b, similar to arms 24a and 24b, have elastic characteristics that enable them to expand somewhat when they are being snappingly fitted over portion 4a of body 4 of infusion assembly 2, and return to their original position after they have been firmly fitted onto portion 4a to thereby securely embrace portion 4a.

For the FIG. 2 embodiment, therefore instead of having to slidably fit forward portion 18 over needle 6 and then onto portion 4a of body 4, a user only needs to snap safety device onto body 4 of infusion assembly 2 by snappingly fitting arms 32a and 32b over portion 4a and arms 24a and 24b over hub 8 of body 4. As was the case with respect to the embodiment shown in FIG. 1, a portion, or all, of the interior surface of base 16 may be coated with an adhesive such as the exemplar epoxy, so that once fitted onto body 4, base 16 will be bonded thereto.

Also similar to the FIG. 1 embodiment, housing 28 is hingedly attached to forward portion 18 of base 16. For the FIG. 2 embodiment, however, there is shown within housing 28 a pair of fingers, or extensions 34a and 34b that may be configured to allow needle 6 to pass, therethrough when housing 28 is pivoted to envelop needle 6, and yet would prevent housing 28 from being removed from needle 6 via a movement in reverse of the direction as indicated by directional arrow 30.

Figure 3:
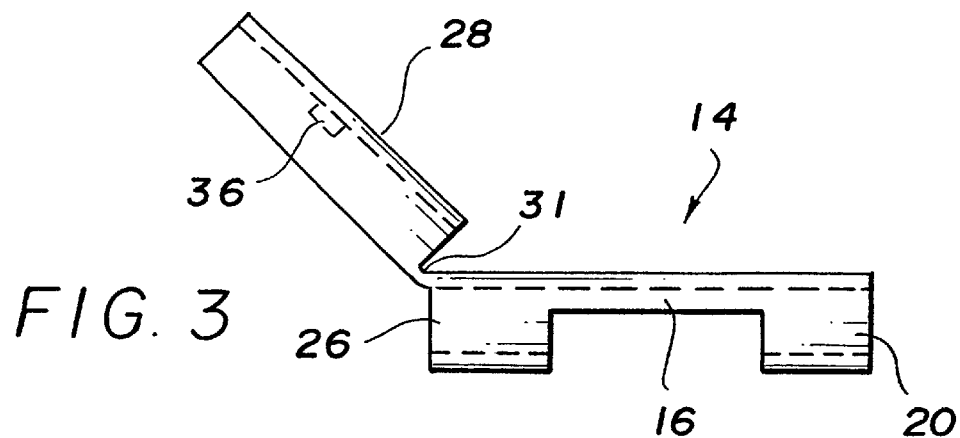
FIG. 3 is a side view of the safety device of the present invention.

FIG. 3 shows a side view of safety device 14 as shown in FIG. 1. Housing 28 of safety device 14 is shown to include a hook 36 integrated within housing 28.

Figures 4A, 4B:
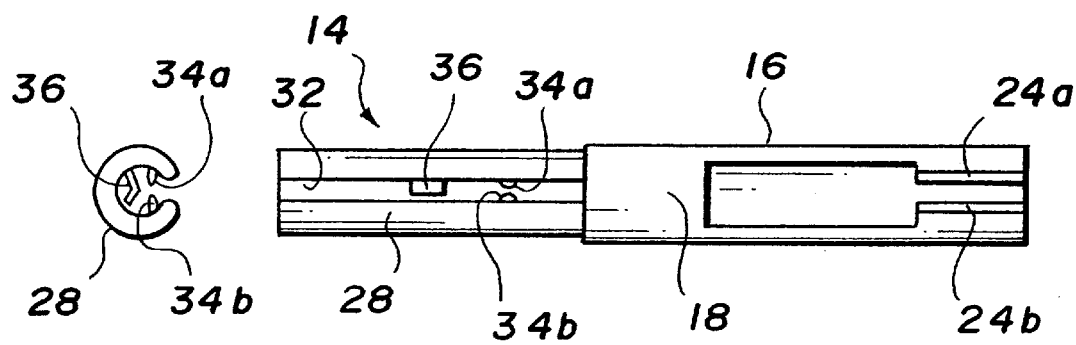
FIG. 4a is a bottom view of the safety device of the present invention.
FIG. 4b is a cross-sectional view of the housing of the FIG. 4a embodiment of the instant invention.

FIG. 4a is a bottom view of safety device 14 of the instant invention, as represented by the embodiment shown in FIG. 1. As illustrated, base 16 includes a tubular portion 18 and a pair of arms 24a and 24b. Attached to base 16 is housing 28 having formed within groove 32 a hook 36 and a pair of fingers 34a and 34b for retaining a contaminated needle of a winged intravenous infusion assembly. Note that even though both hook 36 and fingers 34 are shown, in practice, only one of those locking mechanisms need to be utilized for the instant invention.

Figures 5A, 5B:
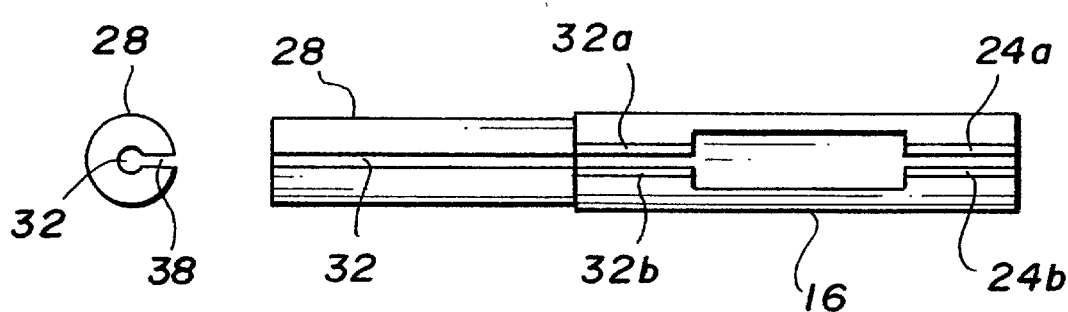
FIG. 5a is a bottom view of another embodiment of the safety device of the instant invention.
FIG. 5b is a cross-sectional view of the housing of the FIG. 5a embodiment.

FIG. 5a is a bottom view of the embodiment of the instant invention as shown in FIG. 2. In particular, base 16 is shown in FIG. 5a to include a pair of arms 32a, 32b and 24a, 24b. So instead of having to slide base 16 over needle 6 and then onto front portion 4a of body 4 of the infusion assembly, a user only needs to snap base 16 onto body 4 of the infusion assembly. The pairs of arms 32a, 32b and 24a, 24b would secure base 16 to body 4 of the infusion device. Housing 28, as shown in the FIG. 5a embodiment, does not have any locking mechanism integrated thereto. This is because, for the FIG. 5a embodiment, groove 32 is configured to have a cross-section that is somewhat smaller than the cross-section of needle 6. Given the elastic characteristics of housing 28, by configuring groove 32 to have a somewhat smaller cross-sectional dimension than that of needle 6, once housing 28 is pivoted to envelop needle 6, needle 6 will be held within groove 32. This is better illustrated in the cross-section view of the housing 28 in FIG. 5b which shows groove 32 to have an exaggerated diameter at the center of housing 28 as compared to passage 38 through which needle 6 passes.

Figure 7:
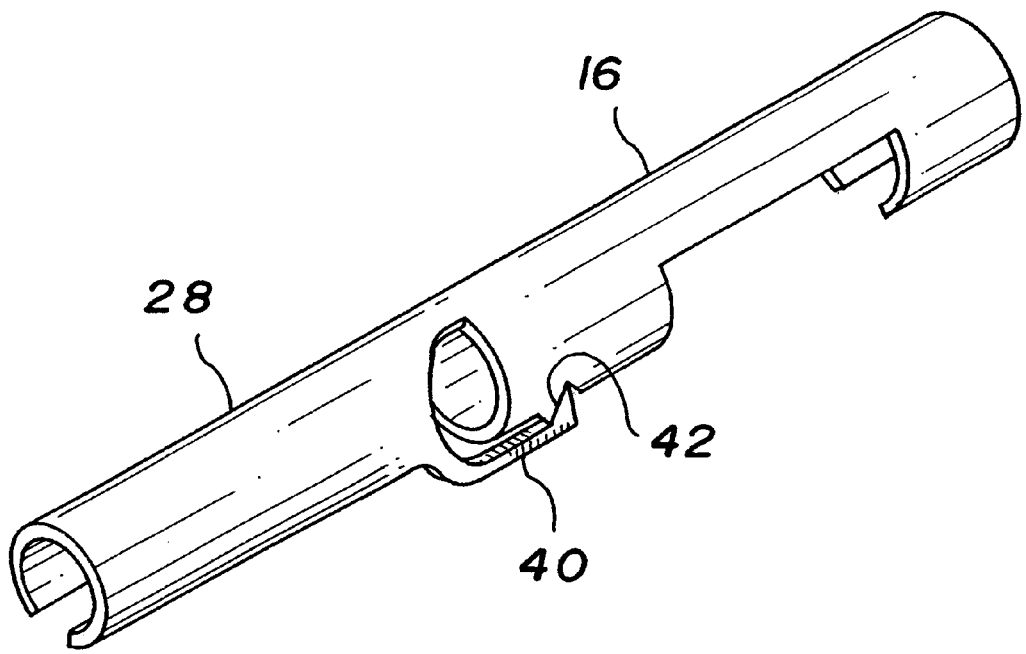
FIG. 7 is a perspective illustration of the FIG. 6 device which housing has been pivoted to a position in alignment along the longitudinal axis of the base.
Figure 6:
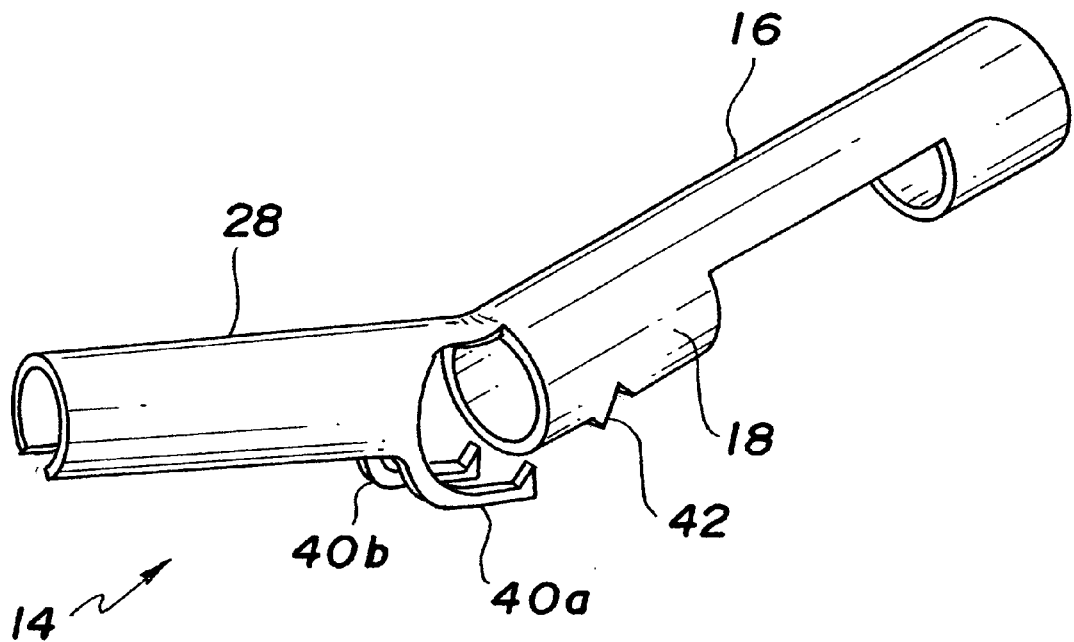
FIG. 6 is a perspective view of another embodiment of the instant invention safety device showing an external locking mechanism comprising coacting locking means at the housing and the base of the device.

FIGS. 6 and 7 are perspective views of yet another embodiment of the safety device of the instant invention. As shown in FIG. 6, safety device 14 has a first locking means, configured as a pair of hooks 40a and 40b, formed externally of housing 28. A corresponding pair of second locking means, represented by only one flange 42, is formed at portion 18 of base 16. Thus, once housing 28 is pivoted into the position in substantial alignment along the longitudinal axis of base 16, hooks 40a and 40b will coact with flanges 42 to thereby fixedly retain housing 28 to base 16, as shown in FIG. 7.

Figure 8:
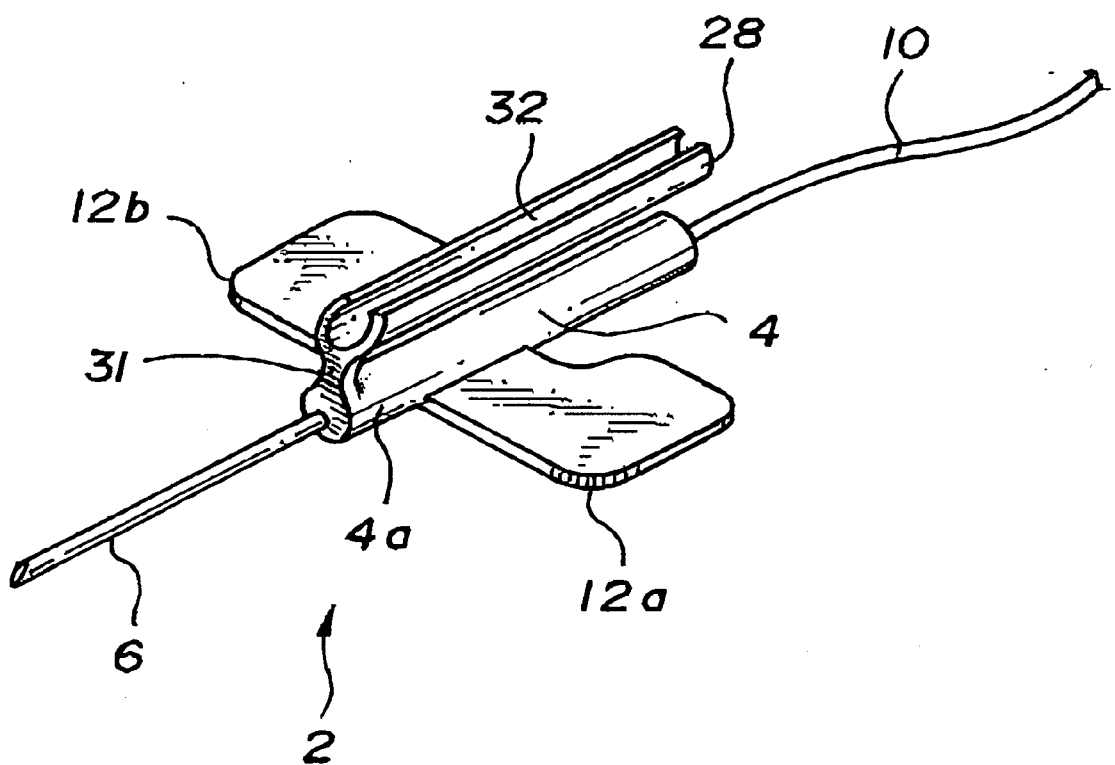
FIG. 8 shows an embodiment of the instant invention in which an IV infusion assembly has molded thereto the safety device as illustrated in the previous figures.

FIG. 8 shows another embodiment of the instant invention in which housing 28 is integrated to body 4 via living hinge 31. This can be accomplished by casting housing 28 and intravenous infusion assembly 2 from the same mold. Although not shown for the sake of simplicity in FIG. 8, the locking mechanisms with respect to housing 28 and its base as shown in FIGS. 2–7 are equally applicable for the embodiment shown in FIG. 8. The one difference is that the coacting locking portion shown in those figures as integrated to portion 18 of the safety device is now integrated to front end portion 4a of body 4.

It should be appreciated that the present invention is subject to many variations, modifications, and changes in detail. For example, in place of the hooks and flanges shown in FIGS. 6 and 7, coacting tabs/openings may be formed at the base and housing of the safety device for providing cooperative means to fixedly retain the base to the housing. Moreover, instead of using hooks and coacting fingers integrated to the housing for retaining the needle once the housing is pivoted to envelop the needle, other types of locking mechanisms may also be used. These include for example the use of a single finger, the use of flaps within the housing or one way valves that would allow the needle to pass into the groove of the housing but yet prevent the housing from further movement relative to the needle once the needle is enveloped by the housing. Thus, it is the intention of the inventor that all matter described throughout this specification and shown in the accompanying drawings be interpreted as illustrative only and not in a limiting sense. Accordingly, it is intended that this invention be limited only by the spirit and scope of the hereto appended claims.

What is claimed is:

1. Safety apparatus to be added to a winged intravenous infusion assembly, said infusion assembly having a needle attached to one end of a body and a hub at the other end of said body, a pair of wings extending from said body between said one and other ends, said apparatus comprising:

a base adapted to be matingly fitted onto said body, said base having at least one pair of arms that firmly embraces a portion of said body or said hub when said base is fitted to said body; and a housing hingedly attached to said base, said housing being pivotable to a position in substantial alignment along the longitudinal axis of said base for enveloping said needle.

2. Safety apparatus of claim 1, further comprising:

locking means integral to said housing for fixedly retaining said needle relative to said housing once said housing is pivoted substantially to said alignment position.

3. Safety apparatus of claim 2, wherein said locking means comprises a hook that snaps over and retains said needle within said housing when said housing is pivoted substantially to said alignment position.

4. Safety apparatus of claim 2, wherein said locking means comprises at least one pair of fingers coacting to prevent said needle from being removed from said housing once said housing envelops said needle.

5. Safety apparatus of claim 1, wherein said base includes at least one locking means and said housing includes at least an other locking means; and wherein said one and other locking means coact with each other for fixedly retaining said housing relative to said base when said needle is enveloped by said housing.

6. Safety apparatus of claim 1, wherein said base includes a pair of first locking means and said housing includes a corresponding pair of second locking means, said first and second pairs of locking means cooperating to maintain said housing relative to said base when said housing is pivoted to said alignment position.

7. Safety apparatus of claim 1, wherein said base is configured to have an interior circumference surface that comes into intimate contact with a substantial portion of the outer circumference surface of said body of said infusion assembly when said base is fitted onto said body.

8. Safety apparatus of claim 7, wherein said interior circumference surface of said base is coated with an adhesive means for bonding said base to said body of said infusion assembly once said base is matingly fitted to said body.

9. Safety apparatus of claim 1, wherein said base comprises two pairs of arms, one of said pairs of arms embracing said hub of said body while the other of said pairs of arms embracing the portion of said body separating said wings from said needle.

10. Safety apparatus of claim 1, wherein said base comprises a tubular portion that slidably inserts over an end portion of said body separating said wings from said needle to thereby matingly fit said base to said body.

11. Safety apparatus of claim 10, wherein said base comprises a pair of arms extending from the end of said base remote from said tubular portion, said pair of arms snappingly fitted over said hub to securely embrace said hub after said tubular portion is fully mated to said end portion of said body of said infusion assembly.

12. Safety apparatus of claim 1, wherein said housing comprises a groove extending substantially along the length of said housing, said groove being dimensioned to have a cross section that is slightly smaller than the cross section of said needle so that when said housing is pivoted to said alignment position, said needle is pressed into said groove and is fittingly enveloped thereby.

13. A method of preventing a contaminated needle of a winged intravenous infusion assembly from being exposed to the environment, said infusion assembly having a body from which said needle extends, a pair of wings extending from said body perpendicularly to said needle, said method comprising the steps of:

mating a safety device to said body of said assembly, said safety device including a base having at least one pair of arms that firmly embraces a portion of said body, said safety device further having a housing hingedly extending from said base; and pivoting said housing to a position in substantial alignment along the longitudinal axis of said base to envelop said needle.

14. Method of claim 13, further comprising the step of:

providing locking means integral to said housing for fixedly retaining said needle relative to said housing once said housing is pivoted substantially to said alignment position.

15. Method of claim 14, wherein said locking means comprises a hook that retains said needle within said housing when said housing is pivoted substantially to said alignment position.

16. Method of claim 14, wherein said locking means comprises at least one pair of fingers coacting to prevent said needle from being removed from said housing once said housing is pivoted to envelop said needle.

17. Method of claim 13, further comprising the step of:

forming a groove substantially along the length of said housing, said groove being dimensioned to have a cross section slightly smaller than the cross section of said needle so that when said housing is pivoted to said alignment position, said needle is pressed into said groove and is fittingly enveloped thereby.

18. Method of claim 13, further comprising the step of:

providing at least one locking means at said base and at least an other locking means at said housing;

wherein said one and other locking means coact with each other for fixedly retaining said housing relative to said base when said housing is pivoted to envelop said needle.

19. Method of claim 13, further comprising the step of:

providing a pair of first locking means at said base and a corresponding pair of second locking means at said housing, said first and second pairs of locking means cooperating to maintain said housing relative to said base when said housing is pivoted to envelop said needle.

20. Method of claim 13, further comprising the step of:

configuring said base to have an interior circumference surface that comes into intimate contact with a substantial portion of the outer circumference surface of said body of said infusion assembly when said base is fitted onto said body.

21. Method of claim 20, further comprising the step of:

coating said interior circumference surface of said base with an adhesive means so that said base is bonded to said body of said infusion assembly once said base matingly fits over said body.

22. Method of claim 13, further comprising the step of:

providing said base with two pairs of arms, one of said pair of arms being provided for embracing said hub of said body while the other of said pair of arms being provided for embracing the portion of said body separating said wings from said needle.

23. Method of claim 13, further comprising the step of:

providing at said base a tubular portion that slidably fits over an end portion of said body to thereby matingly fit said base to said body.

* * * * *